United States Patent [19]

Rosenberg

[11] Patent Number: 4,801,547
[45] Date of Patent: Jan. 31, 1989

[54] DEVICE FOR DETECTING PRESENCE OF MICRO-ORGANISMS IN A SAMPLE

[75] Inventor: Melvyn Rosenberg, Ramat-Gan, Israel

[73] Assignee: Ramot University Authority for Applied Research and Industrial Development Ltd., Tel Aviv, Israel

[21] Appl. No.: 136,666

[22] Filed: Dec. 22, 1987

[30] Foreign Application Priority Data

Jan. 2, 1987 [IL] Israel ......................................... 81145

[51] Int. Cl.⁴ ............................................. C12M 1/26
[52] U.S. Cl. ..................................... 435/292; 435/294; 435/810
[58] Field of Search ................ 435/292, 293, 294, 295, 435/296, 299, 300, 301, 810

[56] References Cited

U.S. PATENT DOCUMENTS

| | | | |
|---|---|---|---|
| 3,282,114 | 11/1966 | Pell | 435/292 |
| 3,563,859 | 2/1971 | Fink | 435/294 |
| 3,762,877 | 10/1973 | Rains et al. | 435/292 |
| 3,875,015 | 4/1975 | Wadley et al. | 435/292 |
| 3,966,552 | 6/1976 | Pagano et al. | 435/294 |
| 4,257,427 | 3/1981 | Bucalo | 435/294 |
| 4,427,634 | 1/1984 | Truglio | 435/294 |

FOREIGN PATENT DOCUMENTS 152368 8/1985 European Pat. Off. ............ 435/292

Primary Examiner—James C. Yeung
Attorney, Agent, or Firm—Benjamin J. Barish

[57] ABSTRACT

A device for transferring a portion of a sample to a culture medium to detect the presence of microorganisms in the sample comprises: a supporting member including two panels hinged together along one edge to permit the panels to assume a folded condition with one panel folded over the other, or an open condition; a culture medium carried on the face of one or both panels facing each other when the panels are in their folded condition; and a transfer member adapted to be supported between the faces of the two panels when in their folded condition and dimensioned such that the opposite ends of the transfer member project from the opposite ends of the culture medium, whereby one projecting end may be brought into contact with the sample to pick-up a part thereof, and the opposite projecting end may be grasped by the user and pulled to move the one end of the transfer member between the contacting faces of the folded panels to transfer and dilute, by smearing, the picked-up sample to the culture medium.

19 Claims, 4 Drawing Sheets

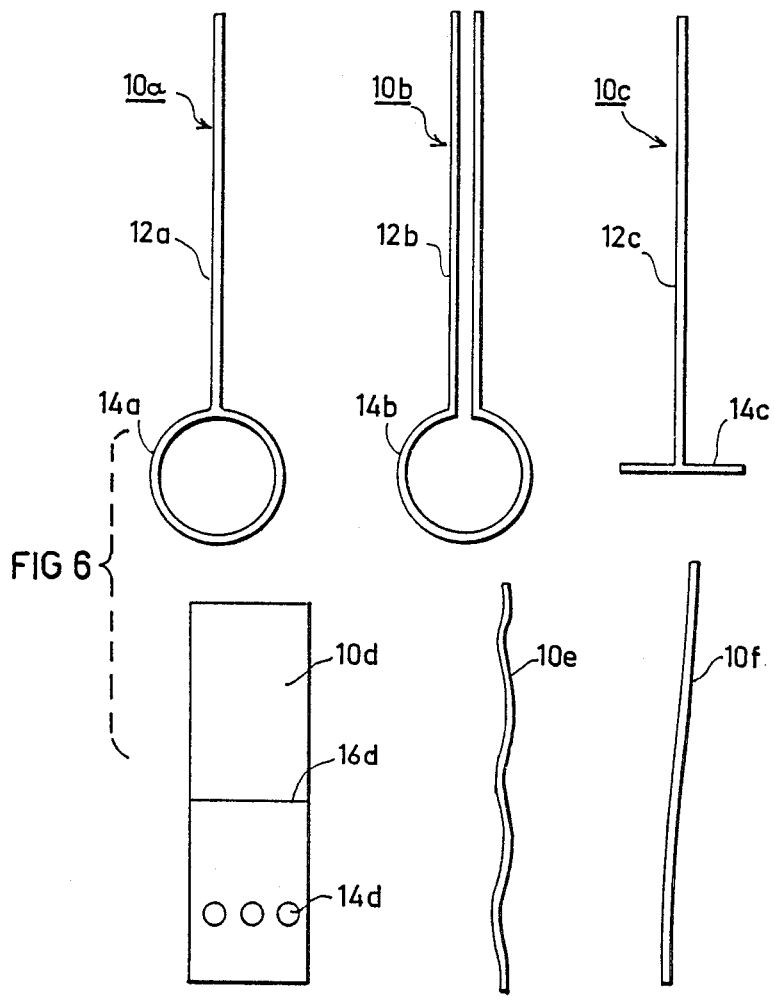

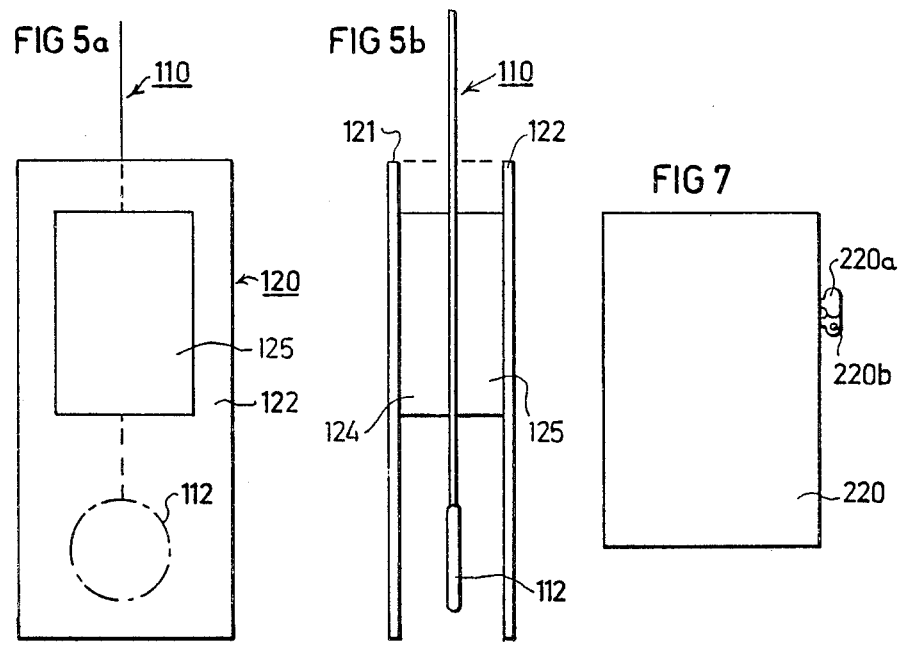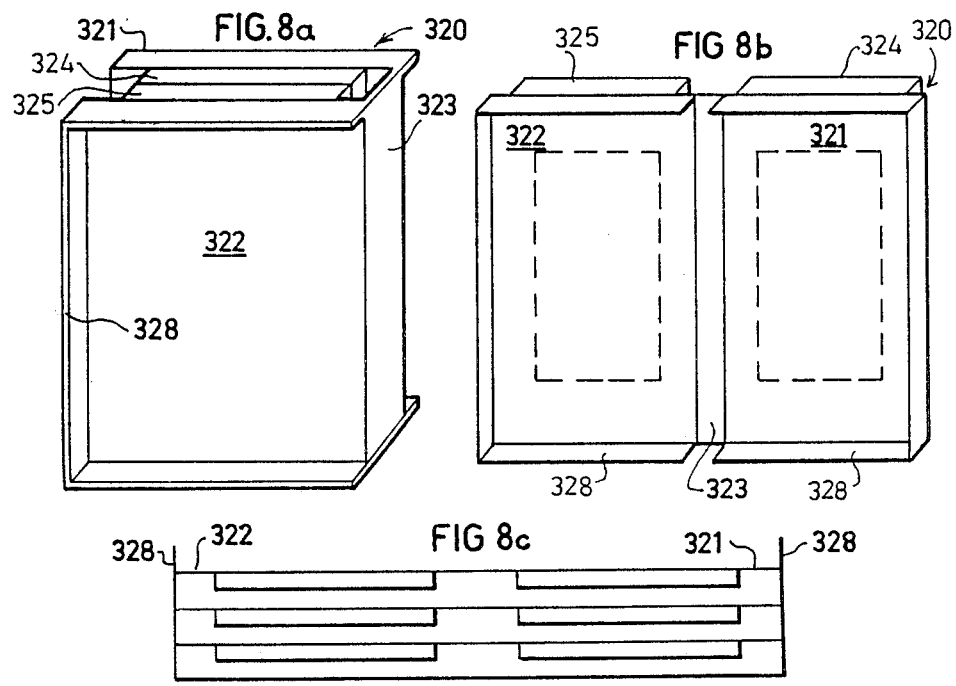

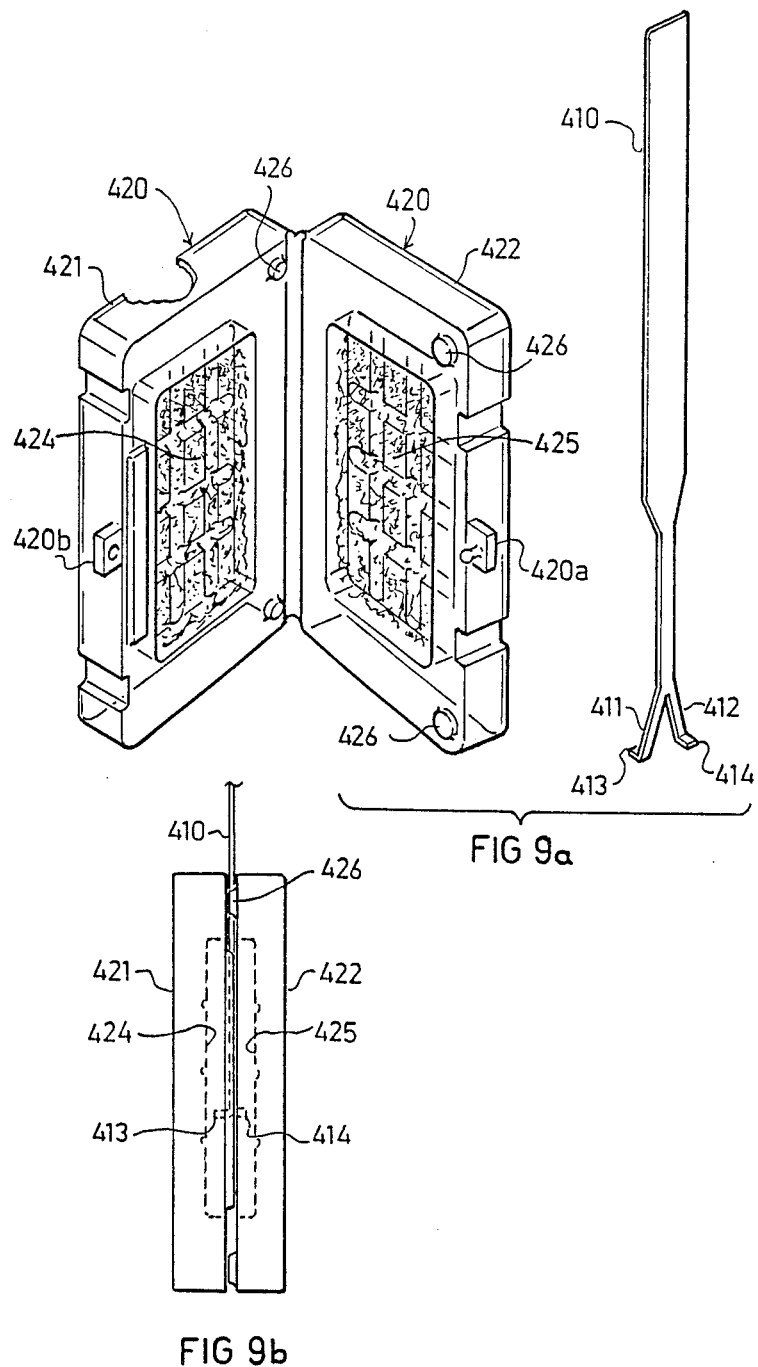

DEVICE FOR DETECTING PRESENCE OF MICRO-ORGANISMS IN A SAMPLE

BACKGROUND OF THE INVENTION

The present invention relates to devices for detecting the presence of micro-organisms in a sample, and particularly to devices for transfering a portion of the sample to a culture medium in order to detect the presence and extent of microbial contamination thereof.

A present method for detecting the presence and extent of microbial contamination of liquids, for example in a urine sample, is by the use of a paddle or dipslide which contains a solid medium on one or both sides. The paddle or dip slide is dipped into the liquid to be sampled, and then is removed, and incubated for microbial growth.

One of the major drawbacks of this method is that individual colonies can only be obtained within a very narrow range of microbial concentrations. Obtaining individual colonies is essential for determining the general identity of each contaminating species, whether there is one or more types of contaminating bacteria. When commercial dipslides and paddles are used for detecting micro-organisms in urine samples, for example, positive urine cultures frequently yield confluent growth, which is difficult to observe, study and transfer for further investigation.

BRIEF SUMMARY OF THE INVENTION

An object of the present invention is to provide a novel device for transferring a portion of a sample to a culture medium which device has advantages in the above respects when used to detect the presence of micro-organisms in the sample.

According to the present invention, there is provided a device for transferring a portion of a sample to a culture medium to detect the presence of microorganisms in the sample, comprising: a supporting member including two panels hinged together along one edge to permit the panels to assume a folded condition with one panel folded over the other, or an open condition; a culture medium carried on the face of at least one of the panels facing the other panel when the panels are in their folded condition; and a transfer member adapted to be supported between the faces of the two panels when in their folded condition and dimensioned such that the opposite ends of the transfer member project from the opposite ends of the culture medium, whereby one projecting end may be brought into contact with the sample to pick-up a part thereof, and the opposite projecting end may be grasped by the user and pulled to move the one end of the transfer member between the contacting faces of the folded panels to transfer, by smearing, the picked-up sample to the culture medium.

It will thus be seen that a device constructed in accordance with the present invention provides a simple and convenient means for transfer and dilution of the sample on the culture medium surface thereby enabling colony isolation, irrespective of the microbial concentration of the sample. After the transfer of the sample to the culture medium, the two panels may be opened to a side-by-side relationship, thereby producing a convenient and compact arrangement for incubation, or otherwise processing, a plurality of the devices at the same time.

In the preferred embodiments of the invention described below, the culture medium is carried on both faces of the two panels facing each other when the panels are in their folded condition, whereby the transfer member transfers a part of the picked-up sample to the culture media on the faces of both the panels. The faces of both panels may carry the same culture medium; alternatively, they may carry different culture media for cultivating different kind of micro-organisms.

The supporting member may be of sheet material, such as plastic, folded along one edge to form the hinge integrally with the panels. According to another arrangement, the supporting member may include two separate panels joined along the one edge by a flexible strip. In all the disclosed arrangements, the two panels may also include a retainer for releasably retaining them in their folded condition.

Further features and advantages of the invention will be apparent from the description below.

BRIEF DESCRIPTION OF THE DRAWINGS

The invention is herein described, by way of example only, with reference to the accompanying drawings, wherein:

FIG. 4 illustrates the supporting member and the culture medium after transfer and incubation of the sample thereto;

FIGS. 5a and 5b are side and bottom views, respectively, illustrating another construction of device for transferring samples to culture media;

FIG. 6 illustrates a number of different types of transfer members which may be used with the device of the preceding figures;

FIG. 7 illustrates a modification wherein the supporting member for the culture media is provided with retainers for releasably retaining the two panels in their folded condition;

FIGS. 8a–8c illustrate a further modification wherein the supporting members are provided with spacer means enabling a plurality of them to be stacked, FIGS. 8a, 8b, 8c, illustrating the device in it closed, open and stacked condition, respectively; and FIGS. 9a and 9b illustrate a further modification, wherein the culture medium is recessed in the confronting faces of the two panels, FIG. 9a being a perspective view of both the supporting member and transfer member, and FIG. 9b being a side view illustrating the manner of using the transfer device.

DESCRIPTION OF PREFERRED EMBODIMENTS

Figure 1:
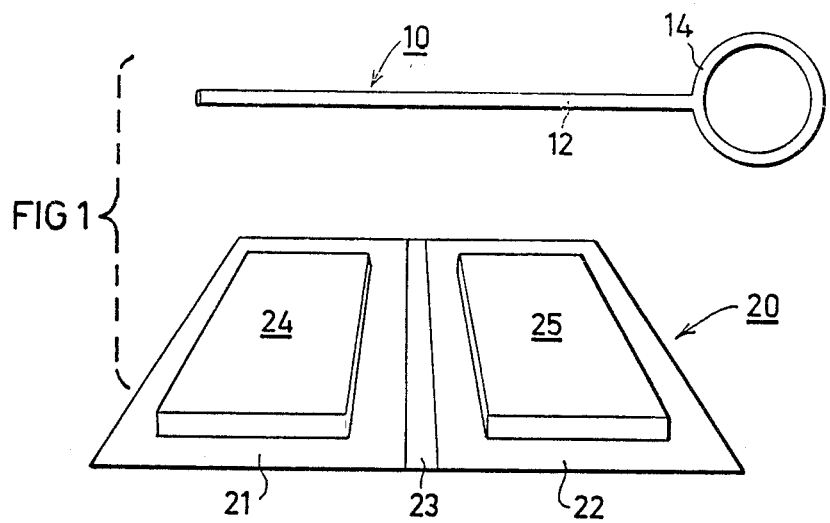
FIG. 1 illustrates the main components of one form of device constructed in accordance with the present invention for transferring a portion of a sample to a culture medium to detect the presence of micro-organisms in the sample.

The main components of the transfer device illustrated in FIG. 1 are: a transfer member, generally designated 10, for picking-up a portion of the sample; and a supporting member, generally designated 20, carrying the culture medium to which a part of the sample is to be transferred.

Figure 2:
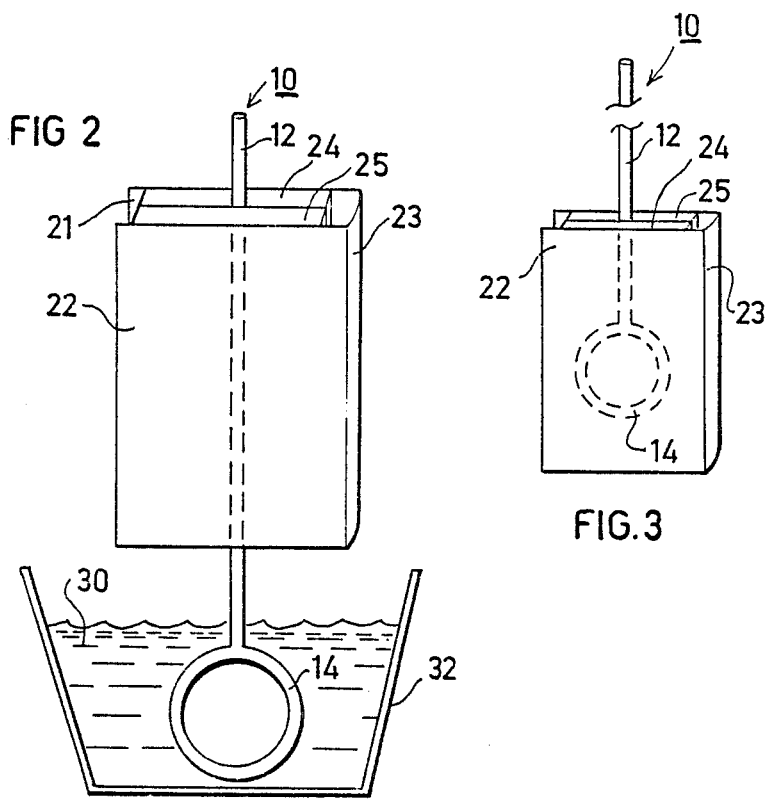
FIG. 2 illustrates the device of FIG. 1 when used for transferring a portion of the sample to a culture medium.

The transfer member 10 illustrated in FIG. 1 includes a flattened handle 12, and a flattened loop 14 at one end for picking up a portion of the sample. The supporting member 20 includes two panels 21, 22 hinged along one edge, as shown at 23, to permit the panels to assume either an open condition as illustrated in FIG. 1, with the two panels in side-by-side relationship, or a folded condition, as illustrated in FIG. 2, with one panel folded over the other. A layer of culture medium 24, 25, is carried on the face of each panel 21, 22 facing the other when the panels are in their folded condition.

As shown particularly in FIG. 2, the transfer loop 10 is adapted to be supported between the faces of the two panels 21, 22 when in their folded condition. In addition, the transfer member illustrated in FIGS. 1 and 2 is dimensioned such that its opposite ends project from the opposite ends of the two panels 21, 22. Thus, the loop 14 projecting from one end of the two panels 21, 22 may be dipped into the sample 30 contained within a container 32; the opposite projecting end of the transfer member, namely the opposite end of handle 12, may be grasped by the user and pulled to move loop 14 between the contacting faces of the folded panels 21, 22 to transfer and dilute, by smearing, the picked up sample to the culture media 24 and 25.

Figure 3:
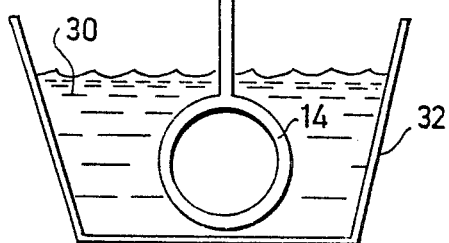
FIG. 3 illustrates the device of FIG. 2 during the transferring operation.

FIG. 2 illustrates the transfer member 10 in its initial condition wherein its loop 14 is dipped within the sample 30; and FIG. 3 illustrates the transfer member being pulled upwardly so as to smear and thus dilute the picked-up sample along the contacting faces of the two layers of culture media 24, 25. The loop 14 is moved for the complete length of the two supporting panels 21, 22 so that when the transfer member is removed from between them, the sample picked-up by loop 14 will have been smeared across the complete lengths of the two culture medium layers 24, 25. The two panels 21, 22 may then be opened, as shown in FIG. 4, and the supporting member may then be incubated or otherwise processed for culturing the micro-organisms deposited on the culture medium layers 24, 25, in order to identify the micro-organisms originally present in the sample.

The culture medium of layer 24 may be the same or different from the culture medium of layer 25. A different culture medium may be used in order to identify different kinds of micro-organisms in the sample.

FIGS. 5a and 5b illustrate a modification wherein the pick-up end of the transfer member 110 does not project from the two panels 121, 122 of the supporting member 120 in the folded condition of the two panels: rather, it is enclosed between the two panels in their folded condition. Thus, the culture medium layers 124 and 125 of the two panels 121 and 122, respectively, are sufficiently thick, and cover only the upper end of the two supporting panels, in order to provide spaces between, the opposite faces of the transfer member 110 and the panels and their culture medium layers 124, 125. In addition, the transfer member 110 is dimensioned so that its pick-up loop 112 does not project through the end of the supporting panels 121, 122, but rather is enclosed by the lower ends of the two supporting panels and spaced from their confronting faces by the culture media layers 124, 125. Such an arrangement provides some protection against contamination of the loop 112 before it is dipped into the sample, while at the same time permits the loop to pick-up a portion of the sample when dipped into it. Alternatively, the loop may be pushed out from between the supporting panels at the time the loop is to be dipped into the sample.

Pulling the transfer member 110 between the two panels 121, 122 of the supporting member 120 will effectively transfer, by smearing, the picked-up sample to the two culture medium layers 124, 125 in the same manner as described above, after which the two supporting panels may be opened and incubated, or otherwise treated, in order to identify the micro-organisms.

FIG. 6, illustrates a number of examples of transfer members that may be used. Thus, transfer member 10a is of the loop-type including a handle 12 and a flattened loop 14; transfer member 10b is similar to that of 10a except that the handle 12b is constituted of the two ends of a wire bent at its mid portion to form the loop 14b. Transfer member 10c includes a straight-wire handle 12c and a cross-bar 14c for picking up the sample.

Transfer member 10d is of sheet material and is formed at its lower end with one or more openings or perforations 14d for picking-up a part of the sample when dipped therein. As one example, transfer member 10d may be of plastic sheet material; and the openings 14d may be calibrated to accept a predetermined volume of the sample, particularly when the transfer member is dipped into the sample to the level indicated by line 16d. Alternatively, transfer member 14d may be of paper or wood calibrated so as to absorb a predetermined volume of the sample when the transfer member is dipped to the level of line 16d.

It will be appreciated that the loops 14a or 14b of transfer members 10a and 10b may be similarly precalibrated to accept a predetermined volume of the sample.

FIG. 6 illustrates two additional forms of transfer members that may be used, namely transfer member 10e in the form of a string, and transfer member 10f in the form of a wire. It will be appreciated that still other forms of transfer members may be used.

FIG. 7 illustrates a further variation wherein the two panels of the supporting member, therein designated 220, are provided with retainers to releasably retain the two panels in their folded condition, preferably with the transfer member (not shown) in between. The retainers for this purpose may be in the form of projections 220a 220b which engage each other when the two panels are closed in their folded condition as illustrated, and which are yieldable sufficiently so as to permit disengagement of the two projections by merely pressing them toward each other, similar to conventional arrangements used in plastic containers for releasably retaining the container lid closed.

FIGS. 8a–8c illustrate further modifications wherein the device includes spacer means enabling a plurality of them to be stacked for sterilization, incubation, storage or other purposes. The device illustrated in these figures, and therein generally designated 320, is basically of the same construction as described above with respect to FIGS. 1 and 2, including two panels 321, 322 interconnected by a hand 323 with each panel carrying a layer of a culture medium 324 and 325, respectively. In this modification, however, an upstanding rim 328 is formed along the outer edge of each of the panels 321, 322. Rim 328 may be, for example, in the form of a flange, continuous rib, or discontinuous rib, formed along the outer edge of each of the panels 321, 322 on the face of the panel opposite to that carrying the culture medium 324, 325. The height of each such rim 328 should be slightly greater than the thickness of the culture media layers 324, 325, so that when a plurality of such devices, in their open condition as shown in FIG. 8c, are stacked one on top of the other, the culture medium 324 of one device will be spaced from the opposite face of the next adjacent device.

In all the described embodiments, the supporting member for supporting the two culture medium layers may be of sheet material e.g., plastic, folded along one edge to form the hinge integral with the panels. This is shown particularly in FIG. 1, wherein supporting panel 20 is constituted of a single plastic sheet folded along the two lines 26, 27 to define the hinge 23 integral with the two panels 21, 22. An alternative arrangement is illustrated in FIG. 5a, wherein the supporting member 120 includes two separate panels 121, 122 joined along one edge by a flexible plastic strip 126 to define the hinge permitting the two panels to be moved either to their open or folded positions.

Experiments have been performed using flat strips of paper, parafilm, plastic material, and various flat metal loops. The flat strips were dipped into urine seeded with *Escherichia coli* alone, or together with *Serratia marcescens*. Agar surfaces were produced by pouring autoclaved agar-containing bacteriological media (brain heart infusion and MacConkey) onto glass slides or petri dishes, and allowing to cool. Each strip or loop was then placed between two agar surfaces and dipped into the liquid sample. The strip was then pulled through the contacting agar surfaces. The agar surfaces were then separated and incubated for microbial growth at 30° C. Results showed that this procedure succeeded in diluting extremely concentrated bacterial suspensions, and provided individual colonies, whereas dipping commercial paddles into the same suspensions resulted in confluent growth.

FIGS. 9a and 9b illustrate a further modification in the transfer device, including a transfer member 410 and a supporting member 420 formed with two hinged panels 421, 422 whose confronting faces are each provided with a layer of culture medium 424, 425. In this case, however, the confronting faces of the two panels 421, 422 are recessed. In addition, panel 422 is provided with circular projections 426 at each of its outer corners. The arrangement is such that when the two panels are closed, as shown in FIG. 9b, the two layers of culture media 424, 425 do not actually contact each other.

The two panels may be releasably retained in their closed, folded condition, by a pair of retainer projections 420a, 420b, similar to the arrangement illustrated in FIG. 7.

The transfer member 410 is in the form of a flat strip of stiff plastic material formed with a pair of arms 411, 412 joined in a Y-formation so as to provide a pair of spaced tips 413, 414 at their outer ends, constituting the pick-up end of the transfer member. Tip 413 is bent in one direction out of the plane of the strip, and tip 414 is bent in the opposite direction, such that the free edge of each tip contacts one culture medium and the juncture edge (juncture with the hand-grasped portion) contacts the other culture medium (FIG. 9b). Thus, after incubation there is produced two streaks of different dilution on each culture medium.

The transfer device illustrated in FIGS. 9a and 9b provides the additional advantages that, when the two panels are closed, their respective culture media do not contact each other, and therefore cannot bleed into each other; and that, after the smearing operation, it is not necessary to open the folded panels before incubation.

While the invention has been described with respect to several preferred embodiments, it will be appreciated that many other variations, modifications and applications of the invention may be made.

What is claimed is:

1. A device for transferring a portion of a sample to a culture medium to detect the presence of microorganisms in the sample, comprising:
   a supporting member including two panels hinged together along one edge to permit the panels to assume a folded condition with one panel folded over the other, or an open condition;
   a culture medium carried on the face of at least one of said panels facing the other panel when the panels are in their folded condition;
   and a transfer member adapted to be supported between the faces of the two panels when in their folded condition and dimensioned such that the opposite ends of the transfer member project from the opposite ends of the culture medium, whereby one projecting end may be brought into contact with the sample to pick-up a part thereof, and the opposite projecting end may be grasped by the user and pulled to move said one end of the transfer member between the contacting faces of the folded panels to transfer and dilute, by smearing, the picked-up sample to said culture medium.

2. The device according to claim 1, wherein a culture medium is carried on both faces of the two panels facing each other when the panels are in their folded condition, whereby said transfer member transfers a part of the picked-up sample to the culture media on the faces of both said panels.

3. The device according to claim 1, wherein said supporting member is of sheet material folded along said one edge to form a hinge integral with said panels.

4. The device according to claim 3, wherein said sheet material is plastic.

5. The device according to claim 1, wherein said supporting member includes two separate panels joined along said one edge by a flexible strip.

6. The device according to claim 1, wherein said two panels include a retainer for releasably retaining them in their folded condition.

7. The device according to claim 1, wherein said transfer member is calibrated to accept a predetermined volume of the sample.

8. The device according to claim 1, wherein the supporting member is formed with spacer means enabling a plurality of the supporting member to be stacked with their culture media spaced from adjacent supporting members.

9. The device according to claim 2, wherein each culture medium is carried in a recess in its respective panel such that the two culture media do not directly contact each other in the folded condition of the panels.

10. The device according to claim 9, wherein the transfer member is a flat strip formed with a pair of spaced tips at its pick-up end, which tips are bent in opposite directions such that each directly contacts one of the culture media during use of the transfer member.

11. A device for transferring a portion of a sample to a culture medium to detect the presence of microorganisms in the sample, comprising:
   a supporting member including two panels hinged together along one edge to permit the panels to assume a folded condition with one panel folded over the other, or an open condition;
   a culture medium carried on the face of each of said panels facing the other panel when the panels are in their folded condition;

and a transfer member adapted to be supported between the faces of the two panels when in their folded condition and dimensioned such that the opposite ends of the transfer member project from the opposite ends of the culture media, whereby one projecting end may be brought into contact with the sample to pick-up a part thereof, and the opposite projecting end may be grasped by the user and pulled to move said one end of the transfer member between the contacting faces of the folded panels to transfer and dilute, by smearing, the picked-up sample to said culture media.

12. The device according to claim 11, wherein said supporting member is of sheet material folded along said one edge to form a hinge integral with said panels.

13. The device according to claim 12, wherein said sheet material is plastic.

14. The device according to claim 11, wherein said supporting member includes two separate panels joined along said one edge by a flexible strip.

15. The device according to claim 11, wherein said two panels include a retainer for releasably retaining them in their folded condition.

16. The device according to claim 11, wherein said transfer member is calibrated to accept a predetermined volume of the sample.

17. The device according to claim 11, wherein the supporting member is formed with spacer means enabling a plurality of the supporting member to be stacked with their culture media spaced from adjacent supporting members.

18. The device according to claim 11, wherein each culture medium is carried in a recess in its respective panel such that the two culture media do not directly contact each other in the folded condition of the panels.

19. The device according to claim 18, wherein the transfer member is a flat strip formed with a pair of spaced tips at its pick-up end, which tips are bent in opposite directions such that each directly contacts one of the culture media during use of the transfer member.

* * * * *